United States Patent [19]

Walker

[11] Patent Number: 4,833,081
[45] Date of Patent: May 23, 1989

[54] BIOREACTOR HAVING CELLS IN BEADS IN A MATRIX

[75] Inventor: Andrew G. Walker, Wantage, England

[73] Assignee: United Kingdom Atomic Energy Authority, London, England

[21] Appl. No.: 186,681

[22] Filed: Apr. 21, 1988

Related U.S. Application Data

[63] Continuation of Ser. No. 909,921, Sep. 22, 1986, abandoned.

[30] Foreign Application Priority Data

Sep. 20, 1985 [GB] United Kingdom ............... 8523327

[51] Int. Cl.[4] .................... C12N 11/04; C12M 1/40
[52] U.S. Cl. .................... 435/182; 435/288; 435/299; 435/177
[58] Field of Search ............... 435/174, 176, 177, 178, 435/180, 182, 284, 288, 313, 299, 300, 301

[56] References Cited

U.S. PATENT DOCUMENTS

| 3,809,605 | 5/1974 | Schmitt et al. | 435/182 |
|---|---|---|---|
| 4,208,482 | 6/1980 | Ehrenthal et al. | 435/178 |
| 4,321,327 | 3/1982 | Chen et al. | 435/177 |
| 4,446,236 | 5/1984 | Clyde | 435/288 |
| 4,518,693 | 5/1985 | Kuu | 435/178 |
| 4,582,799 | 4/1986 | Jarvis | 435/178 |
| 4,603,111 | 7/1986 | Keller et al. | 435/180 |
| 4,647,536 | 3/1987 | Mosbach et al. | 435/178 |

FOREIGN PATENT DOCUMENTS

| 0123326A | 2/1984 | European Pat. Off. . |
| 0130116A1 | 6/1984 | European Pat. Off. . |
| 2083827A | 9/1981 | United Kingdom . |
| 2168721A | 11/1985 | United Kingdom . |
| WO85/01743 | 10/1984 | World Int. Prop. O. . |

Primary Examiner—Samuel Scott
Assistant Examiner—Noah Kaman
Attorney, Agent, or Firm—Larson and Taylor

[57] ABSTRACT

A biochemical reactor including a vessel, a support material matrix in the vessel and particles containing cells entrapped within the matrix is disclosed. In this manner, biological cells that are ordinarily too small to incorporate into a support material matrix can be retained in the matrix by virtue of being grouped into larger particles. Also disclosed is a method for preparing such a biochemical reactor and a process employing the biochemical reactor.

11 Claims, 1 Drawing Sheet

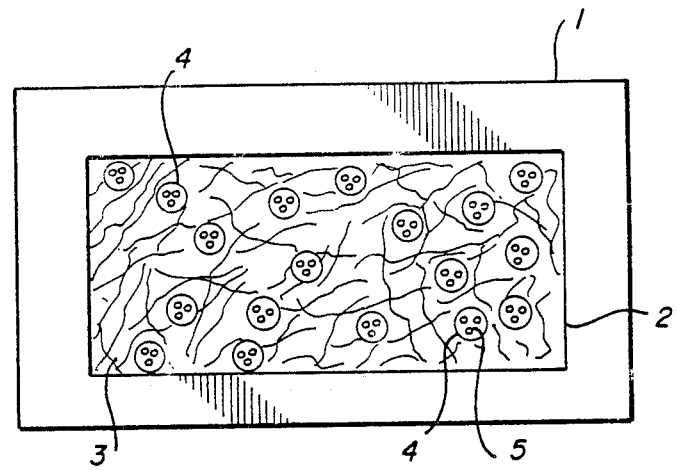

BIOREACTOR HAVING CELLS IN BEADS IN A MATRIX

This application is a continuation of application Ser. No. 909,921 filed Sept. 22, 1986 now abandoned.

RELATED APPLICATIONS

This application is related to applicant's copending U.S. application Ser. No. 06/909,922, filed Sept. 22, 1986 now abandoned which is hereby incorporated by reference.

BACKGROUND OF THE INVENTION

The present invention relates to biochemical reactors containing immobilised biological cells and the preparation of chemical compounds by the use thereof.

SUMMARY OF THE INVENTION

The invention relates to a biochemical reactor which includes a vessel, a support material matrix in the vessel and a plurality of particles retained in the support material matrix. Each particle contains a plurality of biological cells therein.

In another embodiment, the invention relates to a method for the preparation of a biochemical reactor. The method involves introducing particles containing a plurality of biological cells into a support material matrix to thereby retain particles containing biological cells in the support matrix. A vessel is provided around the support material matrix and the retained particles containing biological cells.

In a third embodiment, the invention relates to a process for preparing a chemical compound employing the biochemical reactor of the invention.

BRIEF DESCRIPTION OF THE DRAWING

The single FIGURE is a diagrammatic representation of one form of biochemical reactor in accordance with the present invention.

According to one aspect of the present invention there is provided a biochemical reactor comprising a vessel, a support material matrix in the vessel and a plurality of particles retained in the support material matrix, said particles each containing a plurality of biological cells.

The biological cells may be, for example, eukaryotic cells (e.g. animal cells) or prokaryotic cells.

The particles may comprise, for example, a gel with cells distributed and retained therein. The particles may be fabricated to have a size in the range of, for example 50 to 2000 $\mu$m diameter. Particles containing a plurality of biological cells may be fabricated, by way of example, by culturing cells to a desired point in their growth cycle and then incorporating them into a gel bead (e.g. of agarose). It will be appreciated that the gel should be such as to allow desired chemical species to pass to and from the cells (e.g. to allow nutrients to pass to the cells from a process liquid and to allow cellular products to pass from the cells to the process liquid).

By way of example, the particles may be formed by distributing cells in a molten material (e.g. agarose), forming the resulting mixture into droplets (for example in an immiscible liquid (e.g. an inert oil) or as stable droplets in air) and cooling the droplets to form gel particles containing cells.

Co-pending application Ser. No. 909,921 of even date herewith discloses inter alia that biological cells (e.g. plant cells) may be entrapped and retained in a support material matrix and the matrix contained in a vessel thereby to give a biochemical reactor.

The support material matrix may be, for example, a polyester fibre (e.g. such as wadding used in anorak insulation) or polyurethane foam.

Difficulties may be encountered when seeking to entrap and use small cells in a biochemical reactor as disclosed in the co-pending application hereinbefore mentioned.

Thus, in order to entrap small cells (e.g. animal cells of the order of 10 $\mu$m it is necessary to use a support material matrix with porosity/pores of such small size that flow through the support material matrix is hindered during loading of cells into the support material matrix. Furthermore, during operation contact between the cells and process liquid is restricted with a resulting loss in efficiency of the biochemical reactor.

In accordance with the present invention a plurality of small cells may be incorporated in a particle the size of which particle can be chosen to be sufficiently large such that the particle can be entrapped (as hereinafter defined) in a material matrix which has a porosity/pore size which is large enough to allow satisfactory loading of particles and passage of process liquid.

The particles also have the advantage that they do not grow after entrapment and thus the operational characteristics of the biochemical reactor should exhibit some stability. Growth of the cells in the particles may be inhibited by the choice of conditions to hinder or prevent cell division.

The cells within the particles are also protected to some extent from mechanical influence such as high shear which might exist if the process liquid has to be moved through the reactor at high flow rate.

As used in this specification the term "entrapped" means principally physical enmeshment and excludes gel entrapment or entrapment by growing cell clumps.

According to another aspect of the present invention there is provided a method for the preparation of a biochemical reactor which comprises introducing particles containing a plurality of biological cells into a support material matrix thereby to retain particles containing biological cells in the support material matrix and providing a vessel around the support material matrix and retained particles containing biological cells.

For example, a method in accordance with the co-pending application hereinbefore mentioned may be employed using particles in place of cells. Thus, a fluid composition containing particles containing a plurality of biological cells is introduced onto a sheet of support material matrix and filtered therethrough such that particles are infiltrated into the sheet whilst fluid component of the fluid composition passes through the sheet and is removed therefrom. A second sheet of support material matrix may be placed over the surface of the sheet of support material matrix onto which particles have been deposited, if desired, to provide additional protection for the particles carried in the sheet.

As disclosed in the co-pending application hereinbefore mentioned the reactor may be a thin, flat plate reactor in which case the matrix may be in the form of a thin (approximately 2 to 3 mm) sheet or mat.

Alternatively the matrix may be wound axially to form a "swiss roll" arrangement and placed in a suitably shaped reactor vessel. Referring now to the single FIGURE, there is shown a biochemical reactor 1 having a vessel 2. The vessel 2 contains a support material matrix 3 in which particles or beads 4 incorporating cells 5 are entrapped.

According to a ruther aspect of the present invention there is provided a process for the preparation of a chemical compound which comprises feeding a process liquid to a biochemical reactor, removing process liquid from the biochemical reactor and recovering chemical compound from process liquor obtained from the reactor, said biochemical reactor comprising a vessel, a support material matrix within the vessel and retained by the support material matrix, particles containing a plurality of biological cells.

By way of example the fluid composition containing particles may be distributed evenly over the sheet by means of a spreader bar as disclosed in the co-pending application hereinbefore mentioned.

Where the cells contained in the particles are such that they are capable of excreting an intracellular product (e.g. secondary metabolite) process fluid supplied to the biochemical reactor may contain nutrients such that the cells are encouraged to produce and excrete intracellular products.

If desired the cells may be induced to promote the excretion of cellular products. The cells may be induced to promote excretion by such factors as dissolved gas, ionic concentration, hormonal concentration and pH of the process liquid and osmostic pressure.

As disclosed in the co-pending application hereinbefore mentioned the support material matrix provides an open three-dimensional structure which will permit particles to infiltrate but not to pass straight through. A support material matrix about 2 to 3 millimeters thick having 20 pores per centimeter appears to give satisfactory results. However, it will be appreciated that the optimum porosity of a given support material matrix will depend upon the particles being used. Thus for example support matrix materials with for example 100 to 10 pores per centimeter may be used in thicknesses for example varying between 1 mm and 10 mm.

In the co-pending application hereinbefore mentioned biochemical reactors are disclosed with reference to FIGS. 1 and 2 thereof. Biochemical reactors thus described may be used in accordance with the present invention using particles in place of cells.

EXAMPLE

Mouse Hybridoma cells capable of producing monoclonal antibodies were dispersed in a solution of agarose in PBS (phosphate buffered saline) solution to give a concentration of $10^7$/ml and 1% w/v polymer at 45° C.

The resulting dispersion was formed into droplets by emulsification in a similar volume of cold (4° C.) paraffin oil (BDH). The particles thus formed were washed free of residual oil and suspended in PBS solution (15 g/95 ml).

A procedure similar to that disclosed in the co-pending application hereinbefore mentioned was then followed using particles containing a plurality of cells in place of cells.

Thus, the suspension of particles in PBS solution was, using a sterile bar, dispersed into a thin sheet of polyurethane foam (3 mm thickness, 18×18 cm square) and placed in a vessel thereby to form a reactor as described in the co-pending application with reference to the FIGURE thereof.

The preparation of the beads and reactor was carried out under aseptic conditions.

I claim:

1. A biochemical reactor comprising a vessel, a porous support material matrix in said vessel, a plurality of discrete particles retained in said support material matrix, and a plurality of biological cells, wherein each discrete particle contains a plurality of biologicaal cells incorporated therein, the pore size of said support material matrix and the size of said discrete particles being such that said discrete particles are physically entrapped in said support material matrix.

2. A biochemical reactor as claimed in claim 1 wherein said biological cells are eukaryotic cells or prokaryotic cells.

3. A biochemical reactor as claimed in claim 2 wherein said biological cells are animal cells.

4. A biochemical reactor as claimed in claim 1 wherein said particles comprises a gel with cells distributed therein.

5. A biochemical reactor as claimed in claim 1 wherein said particles have a size in the range 50 to 2000 μm diameter.

6. A biochemical reactor as claimed in claim 1, wherein said particles comprise gel beads having incorporated therein biological cells cultured to a desired point in their growth cycle.

7. A process for the preparation of a chemical compound which comprises feeding a process liquids to a biochemical reactor, removing process liquid from the biochemical reactor and recovering chemical compound from process liquor obtained from the reactor, said biochemical reactor comprising a vessel, a porous support material matrix within the vessel and, retained by the support material matrix, discrete particles containing a plurality of biological cells, wherein the pore size of said support material matrix and the size of said discrete particles being such that said discrete particles are physically entrapped in said support material matrix.

8. A method for the preparation of a biochemical reactor which comprises forming a plurality of discrete particles each of which particles contains a plurality of biological cells incorporated therein, introducing the particles into a porous support material matrix, the size of the particles and the pore size of the porous support material matrix being such that the particles are physically entrapped in the support material matrix, and providing a vessel around the support material matrix in which the particles are entrapped.

9. A method as claimed in claim 8, wherein the said discrete particles containing biological cells are formed by distributing cells in a molten material, forming the resulting mixture into droplets and cooling the droplets to form gel particles containing cells incorporated therein.

10. A method as claimed in claim 9 wherein the mixture is formed into droplets in an immiscible liquid or as stable droplets in air.

11. A method as claimed in claim 9, wherein the molten material comprises agarose.

* * * * *